(12) United States Patent
Maggard et al.

(10) Patent No.: US 6,395,228 B1
(45) Date of Patent: May 28, 2002

(54) SAMPLING AND ANALYSIS SYSTEM

(75) Inventors: Steven M. Maggard, Lake Jackson, TX (US); James H. Higginbotham, Parkersburg, WV (US); Joseph H. Walker, Ashland, KY (US)

(73) Assignee: Marathon Ashland Petroleum LLC, Findlay, OH (US)

( * ) Notice: Subject to any disclaimer, the term of this patent is extended or adjusted under 35 U.S.C. 154(b) by 0 days.

(21) Appl. No.: 08/117,453

(22) Filed: Sep. 7, 1993

Related U.S. Application Data (63) Continuation-in-part of application No. 07/800,788, filed on Nov. 27, 1991, now abandoned.

(51) Int. Cl.$^7$ ............................................. G01N 21/00
(52) U.S. Cl. ................................... 422/82.05; 436/139
(58) Field of Search ....................... 422/82.05; 436/139, 436/140, 143; 250/339, 339.08

(56) References Cited

U.S. PATENT DOCUMENTS

| | | | |
|---|---|---|---|
| 3,505,357 A | | 4/1970 | Jenkins ........................... 73/61 |
| 3,792,272 A | * | 2/1974 | Harte et al. .............. 250/339 X |
| 4,277,326 A | | 7/1981 | Schloeberg et al. .......... 208/263 |
| 4,323,777 A | | 4/1982 | Baskins ....................... 250/339 |
| 4,433,239 A | | 2/1984 | Thompson .................. 250/255 |
| 4,591,718 A | | 5/1986 | Amer ......................... 250/339 |
| 4,612,291 A | * | 9/1986 | Dawes ........................ 436/174 |
| 4,733,965 A | * | 3/1988 | Inman, Jr. et al. ........... 356/326 |
| 4,800,279 A | | 1/1989 | Hiettje et al. ................ 250/339 |
| 4,963,745 A | * | 10/1990 | Maggard ................. 250/339 X |
| 5,145,785 A | * | 9/1992 | Maggard et al. ......... 436/140 X |

FOREIGN PATENT DOCUMENTS

| | | | |
|---|---|---|---|
| EP | 0285251 | | 10/1988 |
| WO | 9115762 | * | 10/1991 |

OTHER PUBLICATIONS

Mark, H. "Advances in Near Infrared Analyzer Technology" Chemical Processing, Feb. 1991, pp. 54–58.*

"The Collins Swirlklean Bypass Filter", Collins Product Company, Livingston, TX.

"Filtrine One Pass Chillers", Bulletin 601–½ 5/89, Filtrin Mfg Co., Harrisville, NH.

"Stainless Steel Filter Housings", Balston Filter Systems Bulletin p. 200K.

"Rating Octane of Gasoline by Near Infrared Spectroscopy", Chemometrics Appl. Note, Infometrix.

"Nondestructive Analytical Proc. for Simultaneous Estimation of the Major Classes of Hydrocarbon Constituents of Finished Gasolines", Kelley et al. Anal. Chem. 1990 62, 1444–145.

Advances in Near Infrared Analyzer Technology Dr. H. Mark & Dr. G. Kemeny, Feb. 1991 Chemical Processing, pp. 54–58.

LT Appl. Note Industry Petroleum, "Determination of Octane Number by NIR," LT Industry Rockville, MD.

"Near–Infrared Reflectance Analysis by Gauss–Jordan Linear Algebra", DE. Honigs, JM Freelin, G.M. Hieftje, TB. Hirschfeld, Applied Spectroscopy, vol. 37, No. 6, 1983.

"Prediction of Gasoline Octane Numbers from Near Infrared Spectral Features in the Kanay 660–1215nm", by JJ. Kelly et al., Analytical Chemistry, vol. 61, No. 4, Feb. 15, 1989.

"Determination of Carbon–Hydrogen Groups in High Molecular Weight Hydrocarbons", A. Evans & R.R. Hibbard, Analytical Chemistry, vol. 23, No. 11, Nov. 1951, pp 1604–1610.

* cited by examiner

*Primary Examiner*—Jeffrey Snay
(74) *Attorney, Agent, or Firm*—Richard D. Stone; Richard C. Willson (57) ABSTRACT

An NIR sampling system designed to provide a stable gasoline sample stream to an NIR analyzer. Preferred design elements include a temperature-controlled stream moving through an inverted coalesce whereby gas bubbles are removed through an overhead stream. Elevated pressure is used to reduce degassing as well. Two or more prototype fuels can be injected to calibrate the instrument over a range and prove accuracy before and/or after analysis of a sample.

7 Claims, 7 Drawing Sheets

SAMPLING AND ANALYSIS SYSTEM

CROSS REFERENCE TO RELATED APPLICATION

This application is a continuation-in-part of USSN07/800,788 filed Nov. 27, 1991 now abandoned.

U.S. patent application Ser. No. 506,391, filed Apr. 9, 1990, now U.S. Pat. No. 5,751,819, relates to the general field of the present invention.

BACKGROUND OF THE INVENTION

1. Field of the Invention

The present invention relates to the field of on-stream analysis, particularly to sampling systems designed to provide stable samples; e.g. of gasoline to an analyzer; e.g., a near-infrared analyzer, commonly class 250, subclass 343 or 341.

2. Description of the Prior Art

U.S. Pat. Nos. 4,575,488 and 3,961,898 each use an on-line analysis instrument with a debubbler upstream to separate bubbles deliberately added between sequential samples.

U.S. Pat. No. 4,963,745 to Maggard et al. determines research, motor, and pump octane by infrared absorbance.

SUMMARY OF THE INVENTION

1. GENERAL STATEMENT OF THE INVENTION

An NIR sampling system designed to provide a stable gasoline sample stream to an NIR analyzer. Preferred design elements include a temperature-controlled stream moving through an inverted coalescer whereby gas bubbles are removed through an overhead stream. Elevated pressure is used to reduce degassing as well. Prototype fuels are a central feature of the present invention and can be injected to calibrate the instrument and to demonstrate or improve accuracy before and/or after analysis of a sample.

2. Utility of the Invention

The present invention is useful for the preferred NIR fiberoptic probes and other NIR probes, but can also be used for salt plates, quartz curettes, transmission cells, and heavy metal fluoride fiberoptic materials; e.g., zirconium fluorides and for other methods of analysis; e.g., colorimetry and infrared, as well as Fourier Transfer Infrared (FTIR). Fourier Transform near infrared can be used. The invention can also be used with multivariate spectrophotometers that are calibrated by developing a correlation between their spectral data and a physical or chemical property by some other primary reference method, e.g. such as a knock engine, GC PIANO, etc. Details of multivariate spectrophotometric calibration techniques for NIR, mid-IR, FT-NIR, and FT-IR spectrophotometers can be found in U.S. Pat. No. 4,963,745 to Maggard; U.S. Pat. No. 5,243,546 to Maggard, and in the references cited therein.

Essentially these techniques involve obtaining spectral data and developing a correlation using a statistical technique such as PLS, principle component regression, or multiple linear regression to develop the correlation between the spectral data and the physical or chemical property data of the samples obtained by some other analytical reference method.

DESCRIPTION OF THE PREFERRED EMBODIMENTS

Figure 1:
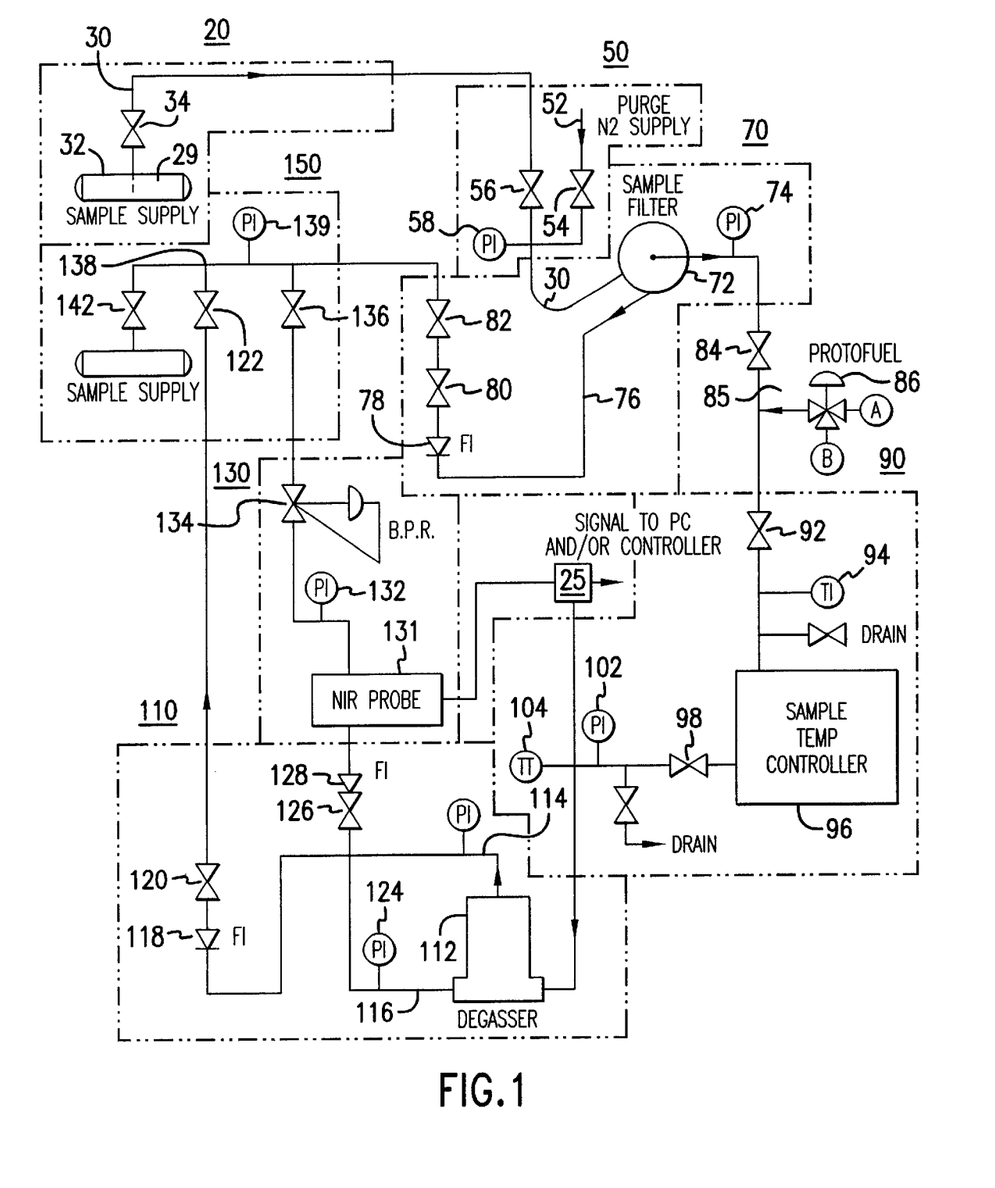
FIG. 1 is a schematic diagram of a preferred sample conditioning system according to the present invention.

In preferred embodiments, the apparatus of the present invention consists of the following major components:

Sample supply means 20 comprising an adduction probe, a control valve and relatively small diameter (for minimum hold-up) tubing (preferably stainless steel) for withdrawing the sample from the stream to be analyzed.

Optional purge means 50 comprising an inward gas (preferably nitrogen) supply and valves and pressure gauges for permitting the purging of the entire system to clear liquids from the system for maintenance purposes.

Optional sample filter means 70 for removing particulates from the sample, said means preferably comprising a self-cleaning, continuous filter means, such as "Swirlklean", Model No. II, manufactured by Collins Products Company of Livingston, Tex., together with suitable pressure gauges, flow indicators, valving and tubing.

Sample temperature controller means 90 comprising an inlet temperature indicator, a temperature controller, such as Filtrine, Model No. PC-50AXP-1LH, manufactured by Filtrine Manufacturing Company of Harrisville, N.H. for controlling the temperature of the sample to the preferred temperature range preferably in the room-temperature range, most preferably approximately 18°–25° C. (65°–75° F.) and additionally comprising suitable drain valves, outgoing temperature indicator, pressure indicator, and the like.

Degassing means 110 comprising a coalesscer, such as the Balston Model No. 45S6, manufactured by Balston Inc. of Lexington, Mass. and suitable flow indicators for rationing the flow through the analysis probe means 130 or back to the sample return means 150. (Alternatively, heating in temperature controller means 90 can precede degassing, and cooling in temperature controller means 90 can be after degassing.)

Analysis probe means 130, manufactured by NIRSystems Division of Perstorp Analytical, Inc., Model OL-5050 of Silver Springs, Md., comprising a chamber for introducing an analytical probe, preferably a near-infrared fiberoptic probe, pressure indicating means, back pressure regulator valve, and the like.

Optional, but preferred sample return means 150 comprising means for collecting both streams from the degasser means and from the degasser means and from the sample filter into a header, which in turn feeds to the stream from which the sample was originally taken by sample supply means 20, but at a point having lower pressure.

Prototype fuel (protofuel) supply means 85 which preferably comprises a plurality of standardized hydrocarbons A and B, etc. analyzed by several different laboratories or matched to a "golden protofuel" so analyzed (by ASTM D2885). More preferably, two or more fuels having different octane (or cetane, etc.) are used as prototypes A, B, etc. The automatic valve 86 opens periodically to inject prototype A and then B sequentially to the NIR analyzer probe 131 (while automatic valve 84 is closed) and calculations are performed and results are automatically logged by the computer, then optionally, the calibrations are adjusted if necessary.

According to the invention, the probe sees a clean, degassed sample of controlled temperature and pressure free from particulate matter. Use of small diameter tubing, preferably less than one inch, more preferably less than one-half inch, and most preferably less than one-quarter inch insures timely delivery of the sample with minimum hold up because of fast flow through the entire sample conditioning system.

Figure 2:
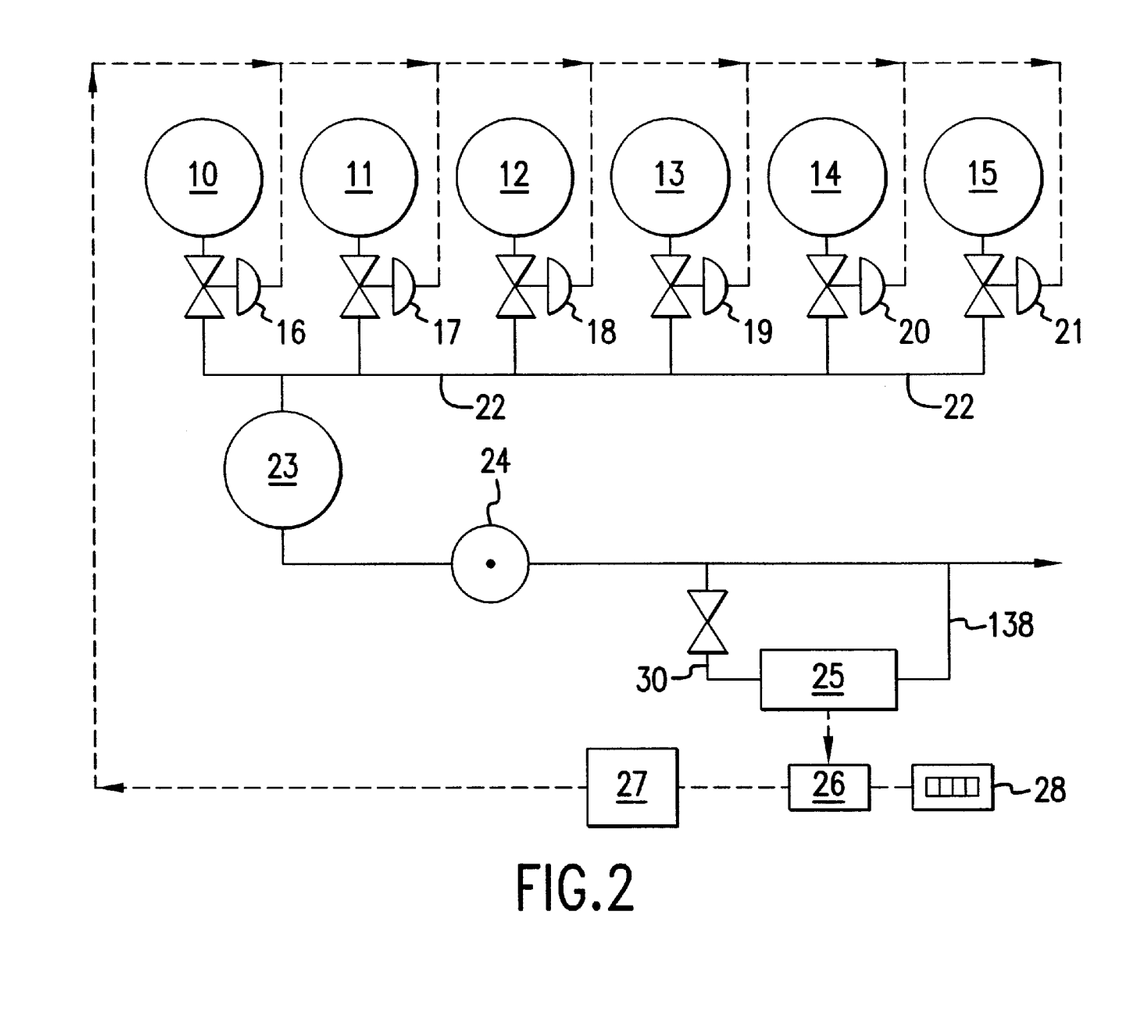
FIG. 2 is a typical gasoline blending system showing various components and particularly showing line 30 leading to analyzer 25 which line 30 is also shown in FIG. 1.

FIG. 2 shows the location of the sample conditioning system. The sample conditioning system is installed along with the "at-line" or "on-line" analyzer 25, also described in U.S. Pat. No. 4,963,745, to S.M. Maggard and assigned to the assignee of the present invention.

EXAMPLE I

Figure 3:
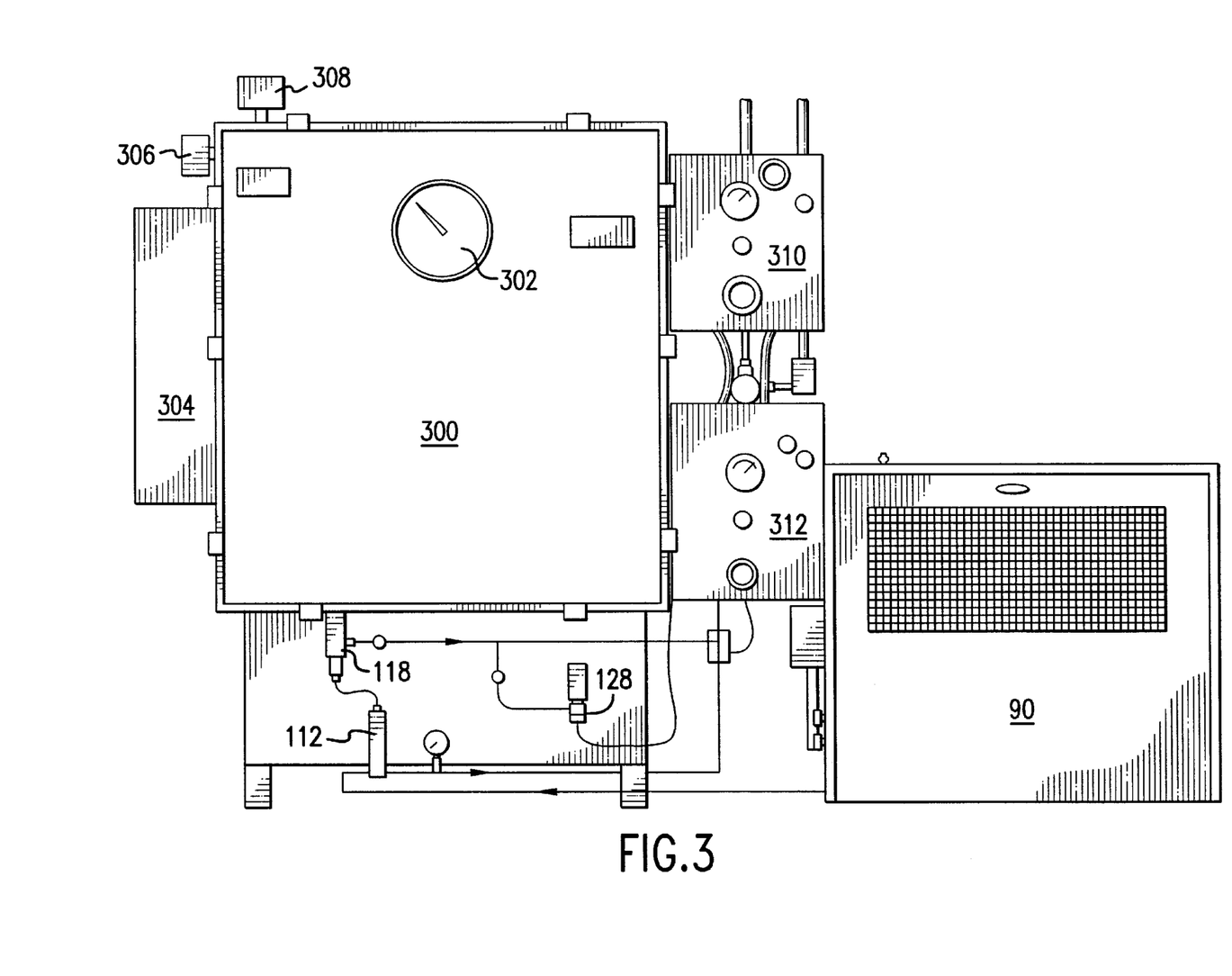
FIG. 3 is an elevation view of the rack and closed cabinet showing the components of the invention in place and also shown in side view in FIG. 3A.
Figure 3A:
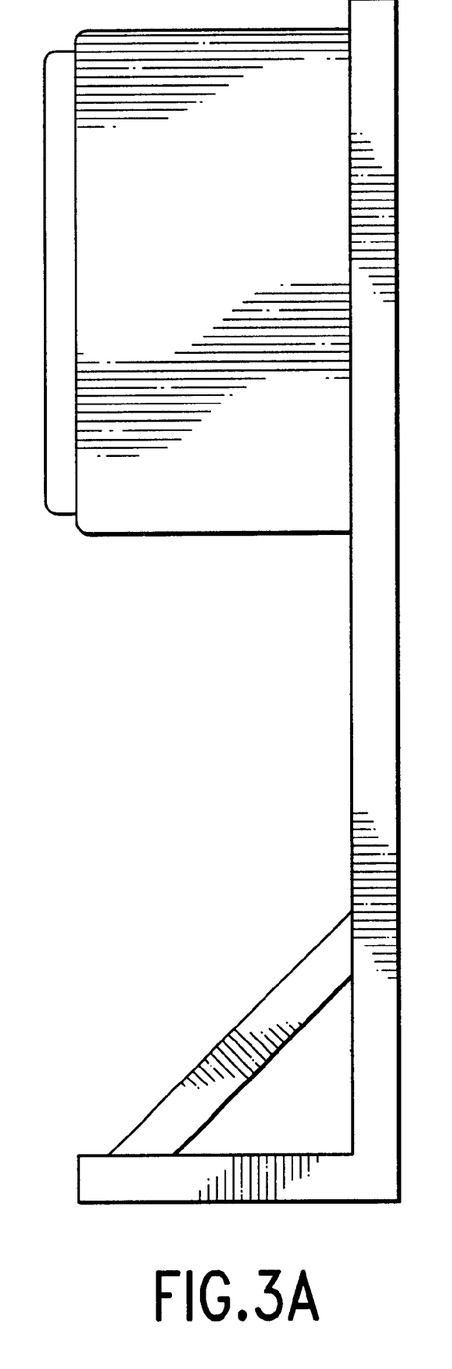
Figure 4:
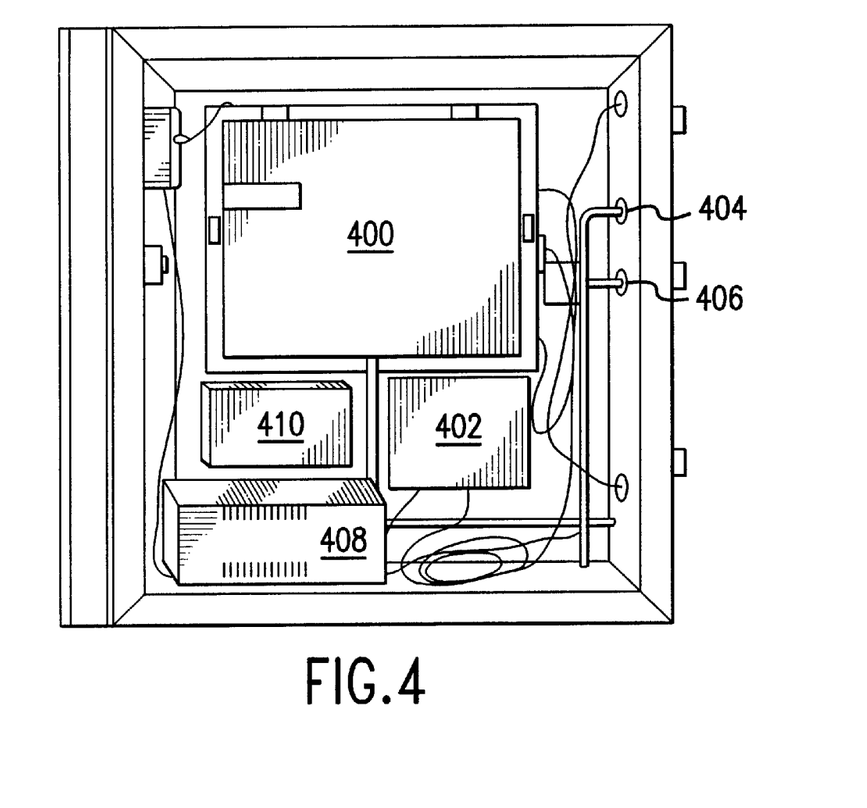
FIG. 4 is a side view of the rack and open cabinet showing the interior elements in place.

Invention According to FIGS. 1, 3 and 4

Referring to FIG. 1, sample supply means 20 includes eduction probe 29 which removes a sample from the approximate midpoint of the main process line and delivers it through sample block valve 34 into line 30, also shown in FIG. 2. Line 30 continues through purge supply means 50 which comprises a nitrogen source, a nitrogen control valve 54, a sample block valve 56, pressure indicator 58, and enters sample filter means 70 which comprises a "Swirlklean" filter 72 (described above) having a capacity of about one gallon/minute. After this sample filter 72, the sample flows through a bypass filter 72 to remove solids from liquid using a small pore membrane on the filtrate side, along with a high speed bypass to provide continuous self-cleaning. After this filter 72 having removed particles larger than one micron, preferably 0.45 micron, the sample flows past pressure indicator 74 and continues on to sample temperature control means 90 with particulates being removed at the bottom via line 76 which flows through flow indicator 78, flow control valve 80 and process block valve 82.

Continuing with the filtered stream 84 flowing into the sample temperature controller means 90, the stream flows past block valve 92, temperature indicator 94 into sample temperature controller 96 which is a prepackaged sample heater/chiller utilizing a high speed single pass flow design for heating/cooling liquids, Model No. PC50AXP-1LH, manufactured by Filtrine Manufacturing Co., and having a capacity of approximately 5 liters/minute, and set for a set point of approximately 24° C. (75° F.), and exits through block valve 98, pressure indicator 102, temperature indicator 104, which is provided with suitable drain valves for maintenance.

The stream flowing from sample temperature controller means 90 into degasser means 110 continues into the degasser 112, a stainless steel filter with replaceable filter elements for removing high solids content from liquids, and exits as a bypass stream 114 which contains most or all of the bubbles entrained into the stream entering the degasser and which flows through flow indicator 118, needle flow control valve 120, block valve 122 into sample return 150.

Because of flammability and explosion hazard in gasoline service, all flow meters are preferably armored, rather than glass or plastic. Particularly preferred is a metallic rotated with a magnetic follower for flow indication. The other stream from degasser 112 is the debubbled stream 116 which flows through pressure indicator 124, flow control valve 126, flow indicator 128, and through analytical probe chamber 131. The NIR probe chamber 131, manufactured by NIRSystems is a 3"×3"×2" block of 304 series stainless steel with ½" 316 series stainless steel Swagloc tube fittings for sample inlet and outlet, and a ¾" 316 series stainless steel Swagloc tube fitting to attach the fiberoptic holder. The analytical probe chamber 131 contains a conventional fiberoptic or other probe for near-infrared or other analytical instrument and permits clean, temperature controlled, particle fee, debubbled flow past that probe for accurate consistent measurement of the analytical properties being measured. The stream continues through pressure indicator 132, back pressure regulator valve 134, block valve 136, and into sample return header 138 which has pressure indicator 139 and block valve 142 (located directly on the main process line) and flows back into the process line at a point somewhat downstream from sample supply means 20 and at a lower pressure than at the sample supply means.

Figure 7:
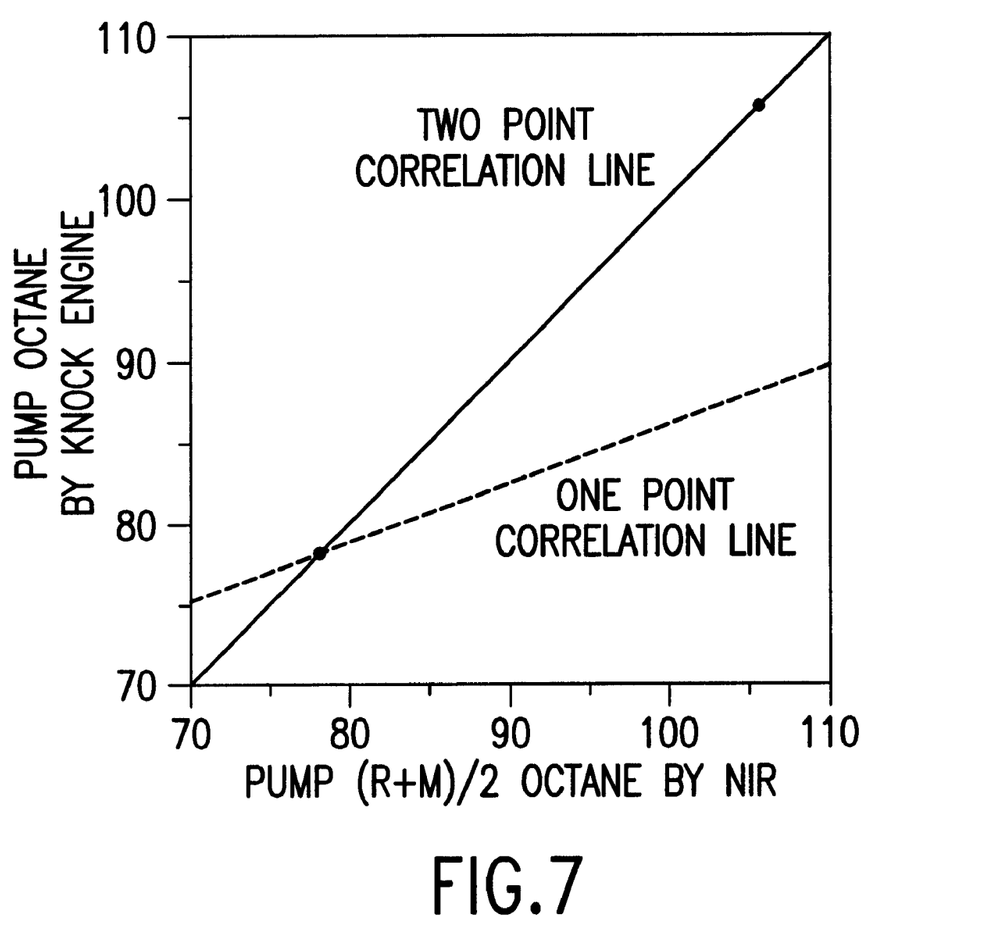
FIG. 7 is a correlation curve of real octane (ASTM/2699/2700) versus octane measured by NIR octane, showing a lower line correlating only a single point and an upper line correlating at two points and hence over an entire range.)

The protofuel injection system 85 comprises automatic valve 86 and protofuel sources A and B, which can be alternatively injected into the sample feed line in place of the sample taken through automatic valve 84 (closed during protofuel injection) from the sample supply 32. Protofuel is a suitable fuel of carefully determined octane (analyzed by ASTM 2699 and/or 2700, preferably by a number of different labs so that the average can be used). By injecting protofuel into the system periodically, the calibration of the system can be checked and standardized for exact accuracy. Stability can also be checked by repeated injection of protofuels. Preferably, two or more separate protofuels are made available so that protofuel A can be injected and then followed sequentially by injection of protofuel B. This provides two points of different octane as shown in FIG. 7. Note that the lower correlation line shows a correlation only at a single point as determined by only a single prototype, whereas the upper correlation line shows a correlation at all points over the entire range as determined by two or more prototype fuels being injected, a substantial improvement over the one-point correlation line because it fixes the correlation curve so that it correlates with values obtained by the ASTM standard knock-engine method, over the entire octane range. More preferably, three or more prototype fuels are analyzed, so the correlation curve need not be a straight line; although a straight line has been found to often be an excellent approximation, based on extensive commercial use.

Unknown prior to this work was that it was possible to adjust a multivariate calibration equation derived from correlating tens to hundreds of samples of known chemical or physical properties to their corresponding spectra data by using as few as two or more readings on precisely characterized hydrocarbons, such as prototype fuels or protofuels described in ASTM D2885 or pure hydrocarbon compounds.

The adjustment used is the so called slope and bias adjustment taught in U.S. Pat. No. 5,243,546, Example 3.

Referring to FIG. 3, the external appearance of a preferred commercial embodiment of the invention for Division II, Class 2, Area Specification For Flammable Hydrocarbon Service, depicts stainless steel cabinet 300 displaying internal temperature on thermometer 302 with temperature being controlled by air conditioner/heater 304 and conduit connections 306 being provided for RS232 connection (direct or via modem) to a personal computer (PC—not shown) displaying the octane and other variables measured by NIR. External power enters through conduit 308 to the interior of the box. (This system can readily be upgraded to a Division I, Class 1 rating by providing fail-safe automatic shutdown in case of failure of air conditioning, cabinet purging or other critical components.)

Z-Purge pressure regulators 310 and 312 regulate the purge air pressure and flow into the cabinet as required by National Electrical Code, Class I, Division 2, for the electronics box 400 and for the lamp source box 402, respectively. Bypass flow meter 118 and 128 measure the flow as shown schematically in FIG. 1. Degasser 112 eliminates bubbles as also shown schematically in FIG. 1. Sample temperature controller 90 houses the components shown under that number in FIG. 1.

Figure 5:
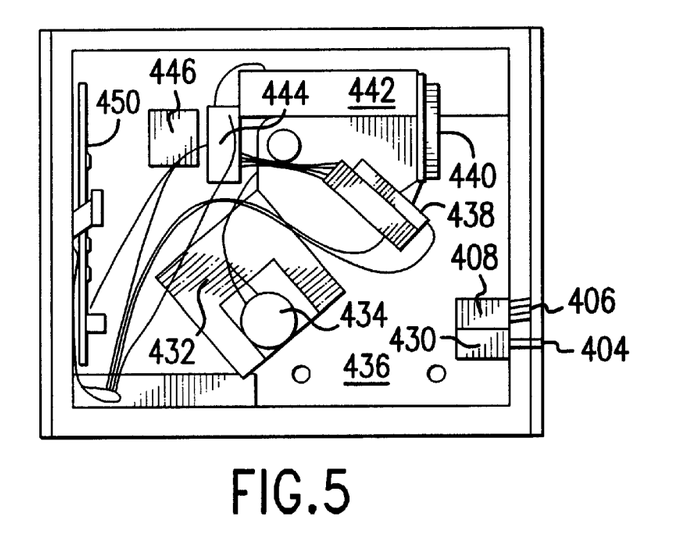
FIG. 5 is a detail of the inner cabinet of FIG. 4.

FIG. 4 shows cabinet 300 with its door open revealing inner NIR instrument cabinet 400 shown in further detail in FIG. 5, lamp 402 which provides illumination through fiberoptic reference cable 404 and fiberoptic sample cable 406. Auxiliary power 408 protects the system electrically and provides and internal voltage regulator plus uninterruptable power supply. Auxiliary power 408 provides a steady 110 volts to transformer 410 which in turn provides 200 volt power supply to the NIR instrument and to auxiliary 12 volt power supply for the lamp 402. The lamp enclosure 402 also includes a solenoid-operated shutter which alternates illumination through the reference fiberoptic cable 404 and then sequentially, through the sample fiberoptic cable 406.

Cables 406 and 404 are held respectively by machined metal block alignment holders 428 and 430 which direct their beams fixedly into monochromator which disperses the light into different orders of the spectrum and into different wavelengths. Thus the monochromator 432 receives, first, the sample fiberoptic light beam 434 and then the reference fiberoptic light beam 436. The sample fiberoptic light beam is conducted by a cable to the sample, and thence reflected back through cable 406 before entering monochromator 432. This instrument arrangement is called "Post Dispersive Transflectance Measurement". (The sampling system could, of course, operate with other types of NIR, infrared, colorimetric or other instrument schemes.)

The order sorter filter 438 also contains a new set of wavelength standards and functions to determine the order in which the wavelengths from the diffraction envelope focus on the detector 440 which outputs an electrical signal to transmission amplifier 442 which passes through various electrical circuits to the housed in 444 and 446, and thence to motherboard 450 which outputs a signal to the PC and/or the process control computer (not shown). This signal preferably meets the standards of RS232 for compatibility with other equipment.

Figure 6:
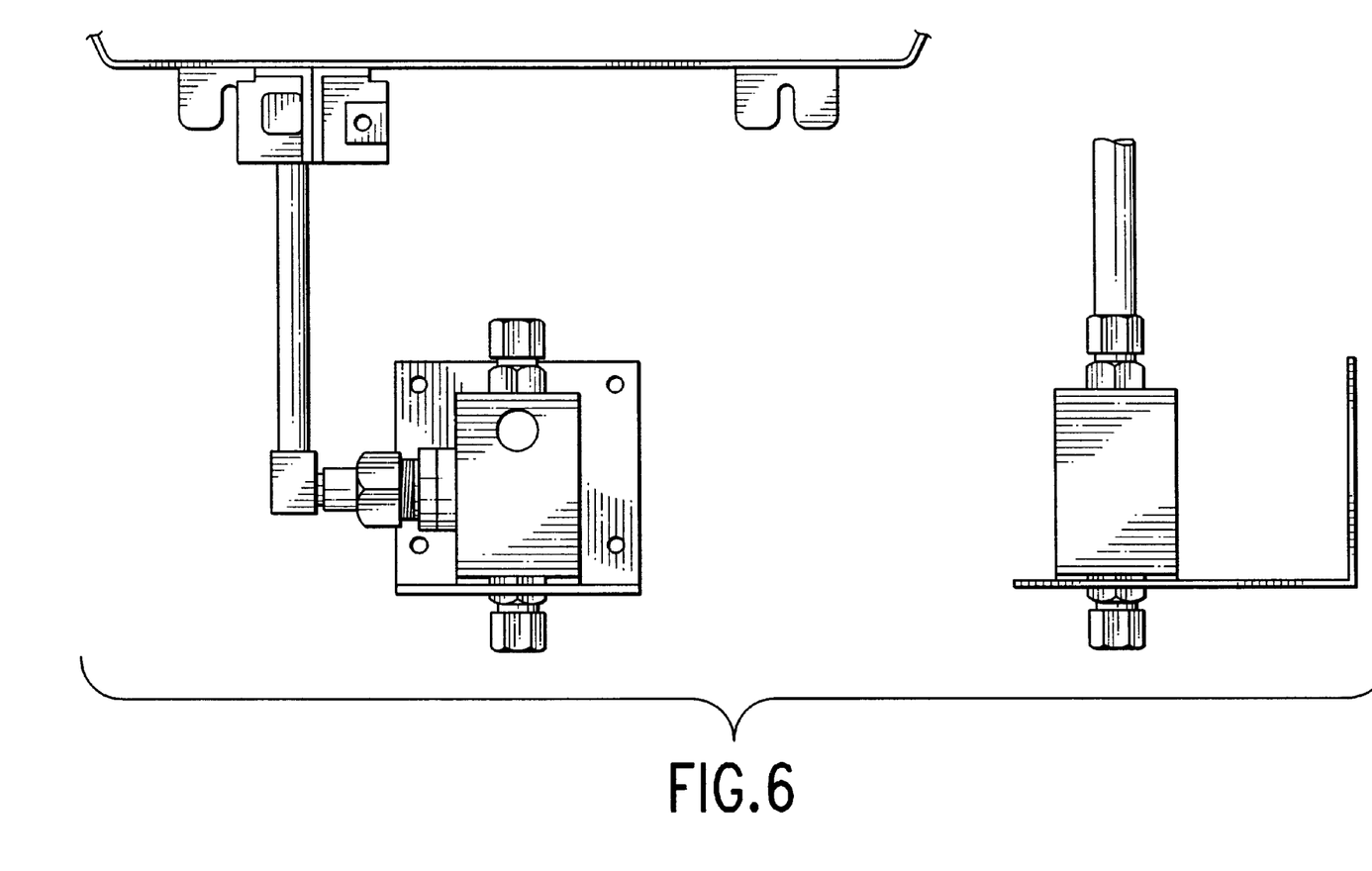
FIG. 6 is a detail of the NIR sample assembly and connection to the fiberoptic cable.

Probe chamber 130, Model DL-6500 or OL-5000, and the connected NIR Analyzer are manufactured by NIRSystems, of Silver Springs, Md. The PIONIR analysis system by Perkin-Elmer can also be suitable for this invention.

EXAMPLE II

Invention Using FTIR

Apparatus similar to Example I, but constructed by substituting an Analect FTIR for the NIR spectrophotometer provides good accuracy in analyzing gasoline and diesel fuels for octane and cetane respectively and functions accurately in a controlled blend system similar to that shown in FIG. 2.

EXAMPLE III

Invention Using a Diode Array Near Infrared Spectrophotometer

Apparatus similar to Example I, but constructed by substituting a Perkin-Elmer infrared spectrophotometer for the NIR spectrophotometer provides good accuracy in analyzing gasoline and diesel fuels for octane and cetane respectively and functions accurately in a controlled blend system similar to that shown in FIG. 2.

EXAMPLE IV

Invention Using Mass Spectrophotometer

Apparatus similar to Example I, but constructed by substituting a Hewlett-Packard mass spectrophotometer for the NIR spectrophotometer provides good accuracy in analyzing gasoline and diesel fuels for octane and cetane respectively and functions accurately in a controlled blend system similar to that shown in FIG. 2.

EXAMPLE V

Invention Using RAMEN Spectroscope

Apparatus similar to Example I, but constructed by substituting RAMEN spectroscope for the NIR spectrophotometer provides good accuracy in analyzing gasoline and diesel fuels for octane and cetane respectively and functions accurately in a controlled blend system similar to that shown in FIG. 2.

EXAMPLE VI

Invention Using GC Mass Spectrophotometer

Apparatus similar to Example I, but constructed by substituting a GC Mass Spectrophotometer for the NIR spectrophotometer provides good accuracy in analyzing gasoline and diesel fuels for octane and cetane respectively and functions accurately in a controlled blend system similar to that shown in FIG. 2.

Modifications

Specific compositions, methods, or embodiments discussed are intended to be only illustrative of the invention disclosed by this specification. Variations of these compositions, methods, or embodiments are readily apparent to a person of skill in the art based upon the teachings of this specification and are therefore intended to be included as part of the inventions disclosed herein. For example, the order of debubbler and temperature control is not critical, though debubbling is preferably downstream of temperature controller. Also, the techniques of copending USSN 698,411 (6379AUS) can be used in conjunction with the protofuel injection by utilizing as at least one of the protofuels a mixture of known amounts of pure hydrocarbon components having octane values calculated from results obtained from a calibrated NIR instrument so that the numbers previously determined for said components can be compared with the numbers obtained by analysis by the system under calibration.

Reference made in the above specification is intended to result in such patents or literature being expressly incorporated herein by reference including any patents or other literature references cited within such references.

What is claimed is:

1. A system for the determination of at least one property of liquid hydrocarbon mixtures by spectral absorption comprising in combination:
   i. a multivariate spectrophotometer operably connected to measure said property;
   ii. at least two sources of reference liquid hydrocarbons having different known values of said property, said sources communicating with;
   iii. prototype injection means for automatically or periodically sequentially injecting a plurality of said reference liquid hydrocarbon mixtures into said multivariate spectrophotometer for calibration of said system over a range of said property;

and additionally comprising in combination the following elements in fluid communication:
   a. sample supply means (20); upstream of the following which are connected in series
   b. sample filter means (70); and
   c. sample temperature controller means (96); and
   d. degassing means (110); all upstream of
   e. analysis probe holder means (130); connected upstream of
   f. sample return means (150).

2. A system according to claim 1 wherein said degassing means 110 comprises a degasser 112 feeding a degassed stream to an analytical probe chamber 130 and outputting a second stream 114 comprising substantially all the bubbles entrained in the incoming stream to be sampled, said second stream being bypassed around said analysis probe holder and returned to the stream being sampled.

3. A system according to claim 1 wherein the analysis probe holder contains a fiber optic probe.

4. A system according to claim 3 wherein the fiber optic probe post dispersive transflectance measurement means.

5. In a system for the analysis of mixtures of hydrocarbons by near infrared absorption, the improvement comprising in combination providing the following elements in fluid communication:
   A. sample supply means; upstream of
   B. sample temperature controller means; and
   C. degassing means; both upstream of
   D. analysis probe holder means containing a fiber optic probe adapted for post dispersive transflectance measurement and operably connected to an infrared spectrophotometer;
   E. prototype injection means for automatically periodically injecting one of at least two hydrocarbon mixtures of predetermined property into said system to provide a reference for calibration of said system over a range;
   F. a plurality of sources of said hydrocarbon mixtures of different predetermined property operably connected to feed said prototype injection means.

6. A system according to claim 5 comprising an on-line system analyzing liquid fuels to determine octane.

7. A system according to claim 5 wherein said hydrocarbon is a liquid fuel and said property comprises octane or cetane.

* * * * *